(12) United States Patent
Bernhard et al.

(10) Patent No.: US 10,458,863 B2
(45) Date of Patent: Oct. 29, 2019

(54) HYBRID VIRTUAL LOAD MONITORING SYSTEM AND METHOD

(71) Applicant: Sikorsky Aircraft Corporation, Stratford, CT (US)

(72) Inventors: Andreas P. F. Bernhard, Shelton, CT (US); James Peter Cycon, Media, PA (US); Alexander I. Khibnik, Glastonbury, CT (US); Mark W. Davis, Southbury, CT (US)

(73) Assignee: SIKORSKY AIRCRAFT CORPORATION, Stratford, CT (US)

( * ) Notice: Subject to any disclaimer, the term of this patent is extended or adjusted under 35 U.S.C. 154(b) by 789 days.

(21) Appl. No.: 13/861,784

(22) Filed: Apr. 12, 2013

(65) Prior Publication Data

US 2013/0275059 A1    Oct. 17, 2013

Related U.S. Application Data

(60) Provisional application No. 61/625,197, filed on Apr. 17, 2012.

(51) Int. Cl.
*G01L 1/00* (2006.01)
*G05B 23/02* (2006.01)
(Continued)

(52) U.S. Cl.
CPC ............ *G01L 1/00* (2013.01); *G01M 5/0033* (2013.01); *G05B 23/0221* (2013.01);
(Continued)

(58) Field of Classification Search
USPC .......................................................... 702/66
See application file for complete search history.

(56) References Cited

U.S. PATENT DOCUMENTS

| 7,532,988 B2 * | 5/2009 | Khibnik ................. G05B 13/04 |
| | | 702/66 |
| 2006/0004499 A1 | 1/2006 | Trego et al. |
| 2011/0245999 A1 | 10/2011 | Kordonowy |

FOREIGN PATENT DOCUMENTS

| DE | 10257793 A1 | 7/2004 |
| EP | 1660958 A2 | 5/2006 |

(Continued)

OTHER PUBLICATIONS

European Seach Report; dated May 17, 2016; 10 pages. Application No./patent No. 13163925.4-1802/2653944.

*Primary Examiner* — Lam S Nguyen
(74) *Attorney, Agent, or Firm* — Cantor Colburn LLP (57) ABSTRACT

Virtual sensors can be used to monitor the loads on the system in determining damage accumulation, remaining useful life or retirement time of the components. A virtual sensor is a mathematical construct to infer a desired system measurement (e.g. a structural load) from readily available system state parameters (e.g. speed, weight, load factors, control settings, etc.). The accuracy of the virtual sensor depends upon the mapping between the desired measurement and the state parameters. A hybrid load monitoring system and method includes one or more direct or physical sensor measurements in addition to the plurality of virtual sensors. Signals from the physical sensors are included as an input (as opposed to an output) to the mapping between system state parameters and the various target sensor feature amplitudes.

18 Claims, 4 Drawing Sheets

(51) Int. Cl.
*G01M 5/00* (2006.01)
*B64F 5/60* (2017.01)

(52) U.S. Cl.
CPC ............ *G05B 23/0283* (2013.01); *B64F 5/60* (2017.01); *G01N 2203/0218* (2013.01)

(56) References Cited

FOREIGN PATENT DOCUMENTS

| EP | 2226766 | A2 | 9/2010 |
| EP | 2333726 | A1 | 6/2011 |
| WO | 2004059399 | A2 | 7/2004 |

\* cited by examiner

HYBRID VIRTUAL LOAD MONITORING SYSTEM AND METHOD

TECHNICAL FIELD

The present invention relates to a system and method of monitoring operational loads on one or more components of a load-bearing system.

BACKGROUND OF THE INVENTION

Many systems experience loads having quasi-periodic properties. For example, equipment containing rotating load-bearing parts (e.g., rotorcraft, jet engines, HVAC chillers, electric motors, etc.) is used in many applications.

To determine when a given part needs to be repaired or replaced, there needs to be a way of calculating the actual rate of wear or damage accumulation for parts that degrade as a function of system usage and loads as opposed to time-based or random damage accumulation. Often it is not practical to physically measure operational loads. In such cases currently known methods use statistical analysis of loads measured in qualification tests of prototype equipment. However, because the actual operational loads experienced by a given part are unknown, the statistical analysis assumes a statistically worst-case damage accumulation for each component to calculate a conservative safe useful life, retirement time or time between overhaul and repair (TBO). These analyses often define calculated retirement times (CRTs) or TBOs in terms of hours of usage assuming a constant rate of wear and damage accumulation per hour of operation. This allows practical time-based maintenance schedules without the need to add numerous physical sensors to the product, which would result in a heavier, costlier, more complex product. However, it results in products either being over designed and/or products that experience average usage and loads being repaired or retired long before they would need to be if CRTs and TBOs could be calculated on an on-going basis using actual operational usage and loads.

If the actual equipment operation is similar to the worst-case assumptions used during design of the components, actual CRTs or TBOs should be close to the a priori conservative CRTs or TBOs based on test data. As a practical matter, however, most equipment will be used in conditions that are much less severe than the worst-case assumptions. For example, a rotorcraft not used in combat will contain parts that will accumulate wear and damage at a slower rate than maintenance schedules assume. Thus, a time-based maintenance schedule would therefore require repair or component replacement earlier than a usage-based maintenance (UBM) system. For example, if a part is designed with CRT of 10,000 hours, a part that has been used for 10,000 hours in mild conditions would probably not require replacement until much later. This causes average equipment to be down for component maintenance even when the component has a significant remaining service life. This unneeded downtime increases equipment operating costs and causes gaps in equipment availability.

Component wear and damage accumulation is highly dependent on the conditions in which the component is used. Because of these varying operational conditions, it would be desirable to monitor the actual loads on a part during equipment use in order to enable usage-based maintenance that would maximize part CRTs and/or TBOs and minimize maintenance costs. This capability would also enable optimized part design and weight management, optimized logistical supply chains, and as well as other applications. This would allow the component CRT to be extended and/or the component to be redesigned to reduce weight while maintaining the same maintenance life for the average equipment. However, the location and operation of the parts may make mounting and monitoring load sensors difficult or cumbersome, particularly for rotating parts, which would require data transmission between a moving sensor and a fixed receiver. Adding load sensors to all of the parts to be monitored increases the complexity of the equipment and requires additional electronics, which increase system weight and cost. It also has a detrimental effect on the complexity and cost of certification of additional equipment for load monitoring.

Virtual sensors were proposed to allow monitoring of actual system operational loads without adding physical sensors to the system and thus enable cost-effective usage-based maintenance (UBM) processes. A virtual sensor is a transfer function that provides a statistically accurate estimate of a desired system measurement (e.g. a structural load) using readily available system state parameters (e.g. speed, weight, load factors, control settings, etc.) as inputs. The accuracy of the virtual sensor depends upon mathematical functions utilized to construct the mapping between the desired measurement and the state parameters. It also depends upon the informally defined quality of the data set utilized to optimize parameters of the transfer function. Such data contain pairs of desired measurements and corresponding state parameters, where pairs could be derived from various sorts of data (e.g. obtained from first principles, simulations, bench or flight tests). When the transfer function is created it is usually tested using blind test to exhibit robust correlations between desired measurements and state parameters.

There are several factors that impact the accuracy of the transfer function. First, even systems that are nominally identical when new (e.g. multiple aircraft of the same model made at different times) may have unintended variations in physical characteristics due to manufacturing variations and changes in the manufacturing process and components over time. Thus, the actual or simulated system which provided data for developing the transfer function may have some differences from the target systems on which the virtual sensors will be eventually implemented and utilized over a significant portion of the system life span.

Additionally, the systems may change over time due to age induced wear and/or modifications (such as hardware additions or modifications). These changes to specific systems will make the predetermined mapping less accurate and increase the variation between systems, which are otherwise nominally identical.

Another possible deficiency of virtual sensors is detecting and handling conditions that are outside of the domains of state parameters that have been mapped and lack of ability to model non-deterministic or random loads due to ballistic impact, severe overload (e.g., hard landing) or other off-design conditions.

SUMMARY OF THE INVENTION

A hybrid virtual load monitoring system and method according to the present invention improves the virtual sensor approach by including one or more direct or physical sensor measurements in addition to one or more virtual sensors comprising a hybrid virtual sensor network. The inputs to the hybrid virtual sensor network include the measured system state parameters. Additionally, physical sensor features are included as an input (as opposed to an output) in the mapping between system state parameters and the various target virtual sensor feature amplitudes.

Some of the factors ("state parameters") that affect load are slowly changing relative to the sample period. For example, in a helicopter application, the total vehicle weight, pilot controls, attitude, torque, etc. all change slowly over time relative to the speed at which samples are taken and control decisions are made. On the other hand, other factors, such as acceleration, have a substantial dynamic component, which changes rapidly compared to the sampling rate. However, even these input state parameters with large dynamic components can be expressed as features (e.g., amplitude and modes) that change relatively slowly over time. In one implementation, the modes that can be derived from the physical sensors are used to decompose the input state parameters with large dynamic components into their features (modes and amplitudes). Even if the physical sensor is not at the same location as the state parameter, it is likely that the modes would be substantially the same (at least for some physical sensors and virtual sensors). Additionally, the modes derived from the physical sensors are used to determine the modes that can be used to represent the loads in the virtual sensors. The modes derived from the physical sensor are also used to decompose the signal from the physical sensor, so that the amplitudes can be used as inputs to the virtual sensor model.

In another possible implementation, the physical sensor measurement can be pre-processed to explicitly compute the feature amplitudes for that physical sensor location (based upon the measured time history and the previously stored feature structure). In this implementation, the physical sensor signals are in essence thus converted to a set of derived system state parameters. The addition of the physical sensor measurement, which is more strongly correlated to the measurements from the virtual target sensors, as an input increases the accuracy of predictions of measurements of the virtual sensor target locations.

Alternatively, or additionally, the physical sensor can be mounted at a virtual sensor location and used to calculate a real time error metric. The error metric is applicable to the collocated physical and virtual sensor location. Additionally, the error metric may be extended to infer/estimate real time error metrics for other virtual target locations. The error metric will indicate if model assumptions have been violated, meaning that the system state at the time of the measurement is outside the range of validity of the virtual sensor model (i.e., outside of the span of operating conditions used for training) or that some other significant system variations such as damaged/worn parts or system configuration changes have occurred.

In another implementation of the hybrid load monitoring system, the physical sensor signal can be used to provide real time updates to the front-end input/output mapping of the virtual sensor algorithm. In this case, the error between the predicted and measured response for the physical sensor location can be used to update the mapping between the system state parameters and the target virtual sensor feature amplitudes. The original structure of the map is defined during the training period. That map can be updated in real time during operation, by comparison of predicted and measured data for the physical sensor. The update may affect the entire map, or alternatively, only the local part of the map related to the physical sensor.

As another implementation, the adaptive update of the mapping can be further expanded to address adaptive updating of the virtual sensor feature structure (modes). This update is performed as long-term error metrics are statistically evaluated over a series of missions. The fundamental ingredient is a re-identification of the feature modes of the physical sensor. This is straightforward because the aircraft state parameters and the actual measurement time history are recorded and available for re-processing. The next step is to propagate the updating of feature structure (modes) for the physical sensor location to the other virtual sensor target locations. This is particularly useful if the system is operated in a new regime or in an existing regime but beyond the original span of the state inputs, neither of which were included in training.

Additionally, or alternatively, analysis of the state inputs and/or the physical sensor measurements can be used to diagnose errors with the mapping between state parameters and feature amplitudes (and adaptively updated, as described above), diagnose errors in the feature modes (and adaptively updated, as described above), and diagnose errors with state parameter inputs.

These and other features of the present invention can be best understood from the following specification and drawings, the following of which is a brief description.

DETAILED DESCRIPTION OF THE PREFERRED EMBODIMENT

Figure 1:
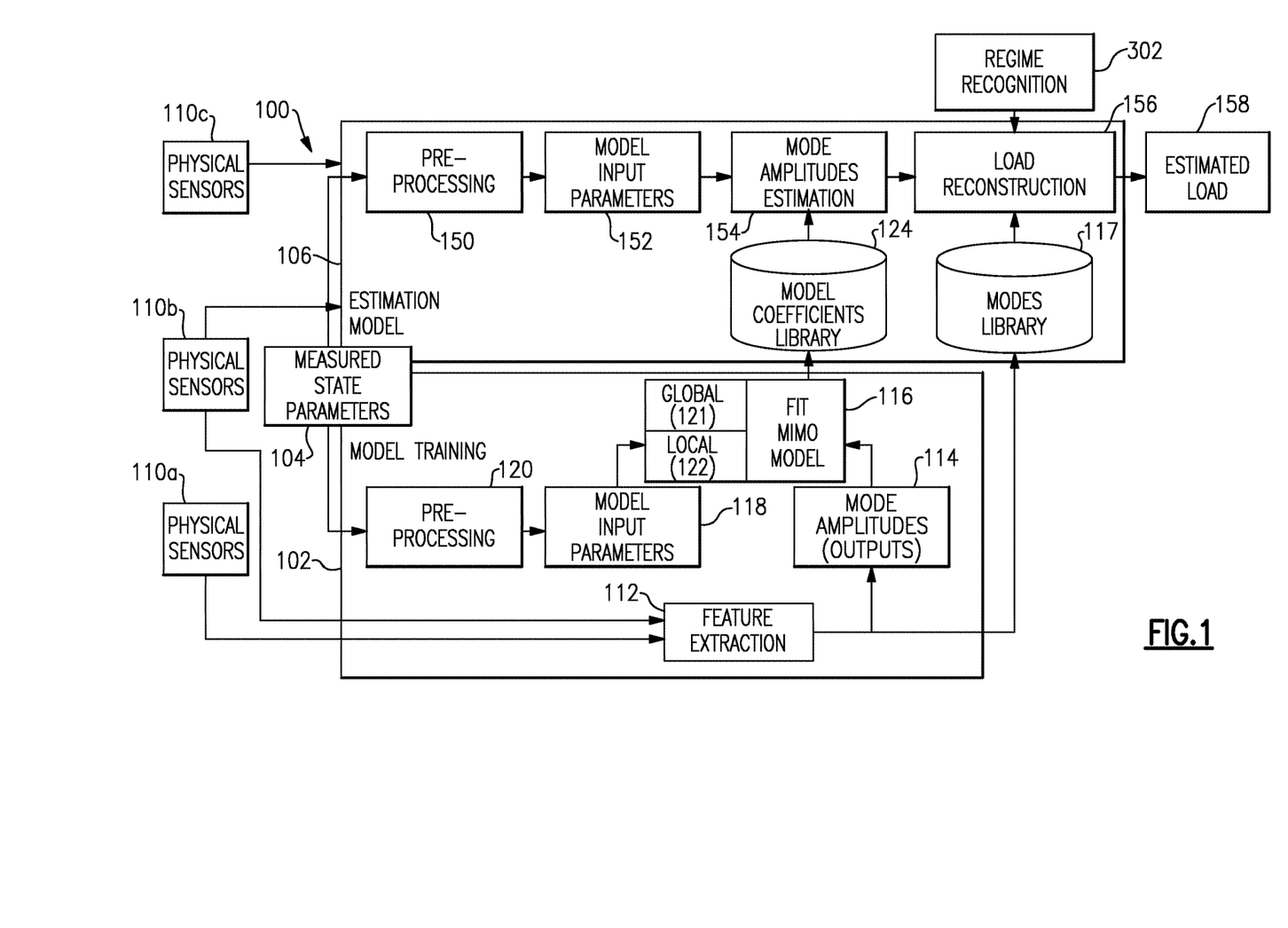
FIG. 1 is a block diagram of a signal estimation process according to one embodiment of the invention.

FIG. 1 illustrates one embodiment of an overall signal estimation system 100 according to one embodiment of the invention. Although the description below focuses on load estimations, it is to be understood that the system and process can be used in any application where accurate signal estimates are desired.

1. Overview of Signal Estimation Concept

Data corresponding to loads applied on a part or a part's response to a load (collectively referred to as "loads" in this application) provides valuable information on how a component is being used. Generally, the system provides an implementation of a mathematical construct that acts as a virtual sensor to infer a measurement of a desired signal, such as a load, from easily available state parameters or other measured loads (e.g., pilot controls, aircraft weight, aircraft attitudes, etc.). The key to virtual sensing is creating a map between the desired signal output and the state parameter and physical sensor signals used as model inputs.

The system identifies fundamental features, such as modes and amplitudes, in the desired measurement and then maps the amplitudes and the modes shapes with the state parameters. The system therefore acts as a virtual sensor that can estimate a desired signal from measured system state parameters and/or physical sensor measurements.

2. Details of Signal Estimation Model Example for Load Monitoring

Referring to FIG. 1, the signal estimation system 100 includes two parts. The first part is model training 102, where the model of the desired estimated output signal (e.g., a model for estimating loads) is obtained through empirical waveforms containing "features" (modes and amplitudes) from measured loads and state parameters 104 obtained during empirical testing. During model training, the state parameters 104 and the measured loads come from the same instances of system operation. In the case of aircraft, for example, the state parameters 104 may include pilot inputs, engine torque, aircraft attitude, rate of climb, vibration, etc. During model training, the measured loads are received from training physical sensors 110a and training/operation physical sensors 110b.

As used in this description, the term "signal" describes any time-variant variable to be estimated. As is known in the art, signals can be directly measurable or obtained from more accessible signals using transfer functions. The term "feature" refers to an element of a feature space that includes characteristics describing the signal of interest. In particular, the complete set of "features" could be used to substantially recreate the signal of interest. The feature space is ideally broad enough to describe various sampled signals corresponding to the same part under different operating conditions. Moreover, as used in this specification, the term "load" encompasses the loads themselves (e.g., mechanical loads, electromechanical loads, electromagnetic loads, etc.) as well as responses (e.g., structural responses, electromechanical responses, electromagnetic responses, optical responses, etc.) to a load; thus, load signals may indicate, for example, force, moment, torque, stress, strain, displacement, velocity, acceleration, current, and/or voltage.

An estimation model 106 is obtained by mapping relationships between the state parameters 104 and the features in measured loads from the training physical sensors 110a and training/operation physical sensors 110b. The estimation model 106 thus acts as a virtual sensor that can infer features in a load signal, and therefore the load itself, from measured state parameters 104 through these features.

The second part is application of the estimation model 106 to new measured state parameters. During equipment operation, measured state parameters 104 are input into the estimation model 106. The state parameters 104 generally are measurable operational parameters of a physical system that describe the temporal behavior or other attributes of the system as a whole rather than providing detailed information about the part itself. The state parameters 104 may also describe an environment in which the system operates. The state parameters 104 are then used to obtain estimated features defining an estimated load signal. The estimation model 106 can then use the estimated features to synthesize a load signal waveform that is an estimate of the actual loads and/or actual responses experienced by the part. More particularly, the estimation model 106 infers a correlation between the state parameters 104 and the load signal.

In one example, the features reflect the load signal over time with respect to various operating conditions. More particularly, the estimation model 106 separates time dependent features, such as mode amplitudes, and time-invariant features, such as mode shapes, and then stores the time-invariant features in a library. Note that the time-invariant features in this example are functions of an azimuth angle defined, for example, over a span of a single revolution of a rotating part. The mode shape reflects many characteristic details of the signal behavior over one revolution, while the mode amplitude reflects signal characteristics that change more slowly over multiple revolutions.

By separating the load estimation system 100 into two separate steps, the system is able to capture most of the key non-linearities in the relationships between the measured state parameters and the load. The two-step process also builds in more information about the relationships between loads and the state parameters 104 by predicting an entire load signal waveform output rather than a single characteristic of the waveform (e.g., peak-to-peak amplitude) as in most previously known methods.

Additionally, loads measured by training/operation physical sensors 110b and operation physical sensors 110c are also input to the estimation model during equipment operation. As shown, training/operation physical sensors 110b are the same physical sensors 110b (or at least, physical sensors at the same location and/or measuring the same loads) that are used in both model training and in operation. The operation physical sensors 110c are physical sensors that are not equivalent (in location, or what load was being measured) to any physical sensors used in model training, but are used during equipment operation. Training physical sensors 110a are physical sensors that were used during training but not during operation.

Figure 1A:
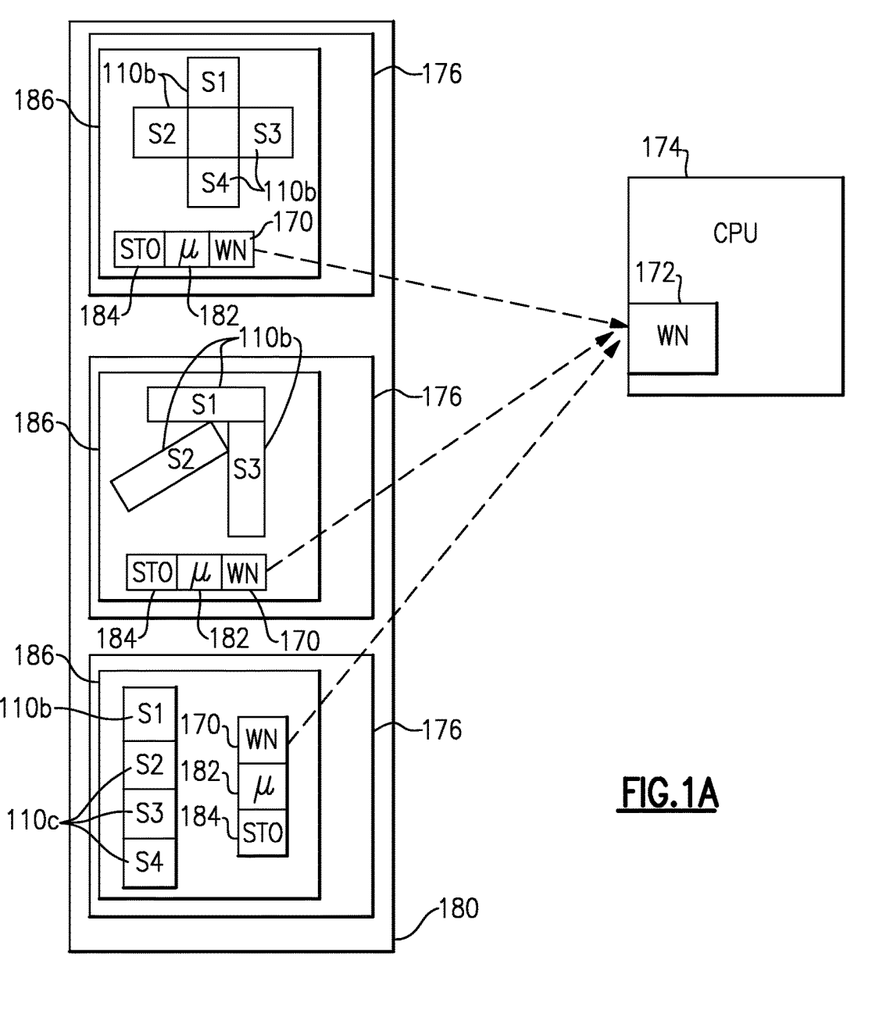
FIG. 1A is a block diagram of one possible implementation of the physical sensors in a wireless distributed network.

Referring to FIG. 1A, the physical sensors 110b-c may be wireless sensors in a distributed wireless sensor network. One or more of the physical sensors 110b-c may be housed together in a housing 186 and mounted to components 176 in the system 180, or the physical sensors 110b-c may be multi-functional sensors, such as sensors that can measure more than one characteristic, such as strain, temperature, humidity, etc. The physical sensors 110b-c are connected to a wireless node 170 having a local processor 182 that processes and locally stores data regarding the measured loads, such as time histories, exceedence logging, FFT amplitudes, load histograms, averages, etc. in local storage 184. The wireless node 170 may be powered locally by a battery in the housing 186. Because the wireless node 170 has local storage 184, there is no requirement to communicate in-flight, which eliminates EMI concerns. After the flight has been completed, a host wireless node 172 instructs all the wireless nodes 170 to check in and transmit their data from local storage 184. The analysis described herein is then performed by CPU 174. The host wireless node 172 and CPU 174 could be on-board or off-board (e.g. a hand-held device). Alternatively, one or more (or all) of the physical sensors 110b-c could be hard-wired to one another and/or to the CPU 174.

Referring to FIG. 1 in greater detail, the model training 102 according to one example may include obtaining measured loads from physical sensors 110a, 110b by instrumenting a part of interest in test machinery, rotating the part, and obtaining output signals from one or more load sensors. Depending on the sensor type and depending upon the particular part, the sensors may be located in load-bearing paths and physically located as close to the part (or a critical location on the part) as possible. However, high load gradients, where slight change in location causes significant errors, should be avoided. The physical sensors 110a, 110b may be placed near key point but in position that has a less severe gradient.

A feature extraction step 112 extracts the features from the sensor outputs. The features themselves may be, for example, mode shapes and mode amplitudes of the output signal from the sensor. Mode shapes correspond to combinations of harmonics or other inherent behavior that is always present in a given load signal, while mode amplitudes act as coefficients for the mode shapes and indicate the influence of each of the mode shapes on the final output signal waveform.

The goal of the feature extraction step 112 is to determine the nature and the number of features that will allow accurate load estimation and to eventually obtain a compact representation of the load through time scale separation, feature extraction and mode truncation. The feature extraction step 112 generally involves conducting shaft-synchronous discretization of the load sensor outputs, transforming the load sensor outputs into a two-dimensional array ("matrix A") parameterized by, for example, azimuth angle (vertically) and revolution number (horizontally). In one example, features are obtained by singular value decomposition of matrix A, where left-handed singular vectors define mode shapes and the product of singular values and right-handed singular vectors define mode amplitudes. Note that this is equivalent to computing eigenvectors and eigenvalues of a covariance matrix $AA^T$, where $A^T$ is the transposition of A. In this case, normalized eigenvectors play a role in the mode shapes, and the projection of A onto each eigenvector becomes the corresponding mode amplitude. Eigenvalues represent energy level contained in each mode. Using singular vectors or equivalent eigenvectors of the covariance matrix described above as mode shapes allows minimization of the number of features needed to estimate load sensor outputs accurately.

Figure 2:
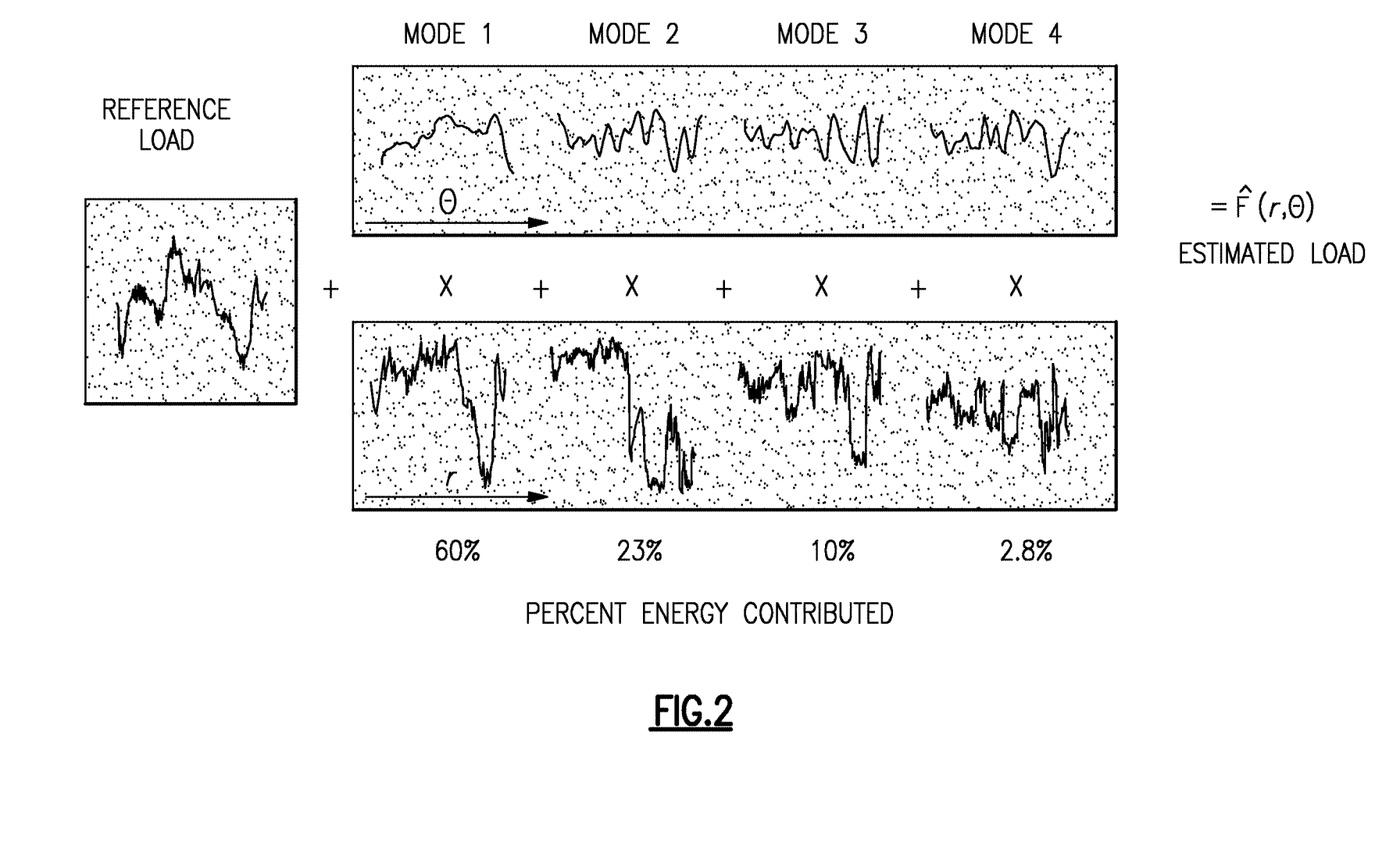
FIG. 2 illustrates an example of features in a signal.

FIG. 2 illustrates one example of the relationship between the output signal of the load sensor and its features. This relationship is used to both extract the features from the load sensor as well as to reconstruct estimated signals from features derived from measured state parameters 104. In one embodiment, the relationship between the state parameters 104 and the mode amplitudes is in the form of a linear map, such as a multiple linear regression model, but other relationships (e.g., general linear models or nonlinear models such as neural network models, state space models, etc.) are possible. The relationship may be shaped or otherwise modified through, for example, specific selection, filtering, smoothing and/or weighting of the inputs and outputs.

In this example, each time-invariant feature represents one full revolution of the shaft and is derived from analyzing the measured load signal from one of the physical sensors 110a, b. More particularly, each time-invariant feature is a specific waveform corresponding to a sequence of loads that a given part experiences during one shaft revolution. For example, in the case of rotating blades in a rotorcraft, the blades will experience different loads when they sweep into an oncoming airstream as opposed to when they sweep away from the same airstream. Thus, there will be a definite pattern reflected in the load signal over one rotation/cycle. In other words, the load signal is analyzed over a discrete time segment comprising one revolution of the shaft. Note that it is also possible to extract features over another fixed interval in the azimuth angle domain rather than a full revolution.

As noted above, the measured load from each of the physical sensors 110a, 110b signal is represented through mode shapes and mode amplitudes. The mode shapes, are in the azimuth angle domain $\Theta$, while the mode amplitudes 114, which correspond to the strength of each mode shape, are in the revolution domain r. Represented mathematically, a given load signal $F(r,\eta)$ may be approximated by another signal $\hat{F}(r,\theta)$ (load estimate) having the following form:

$$\hat{F}(r,\theta) = C_0(r) + C_1(r)\Phi_1(\theta) + C_2(r)\Phi_2(\theta) + \ldots + C_M(r)\Phi_M(\theta)$$

where $\Phi(\Theta)$ is the mode shape, $C(r)$ is the mode amplitude, and M is the number of modes that are being used in the estimation model. Note that the first term in the sum does not include mode shape; this is because this mode shape is assumed to be a constant function of $\Theta$.

As shown in FIG. 2, the load signal $F(r,\Theta)$ is simply the sum of a reference load $\Phi_0(\Theta)$ and terms containing the product of mode shapes and their associated mode amplitudes. Each mode shape has a corresponding energy level represented by the integral of mode amplitudes 114, whose values are driven by the state parameters 104. The energy level for a particular mode shape, expressed as a percentage of the total energy equal to the sum of energies of individual modes, is a convenient aggregate measure of the mode's importance and influence in the estimated signal. Mode shapes act as functions in a given signal, while the mode amplitudes 114 act as coefficients for the mode shapes and reflect the unique shape of the signal. Because the mode amplitudes 114 are driven by the state parameters 104, it is possible to both distill unique mode amplitudes 114 from a measured load associated with a given set of state parameters 104 and to estimate mode amplitudes 114 corresponding to a set of state parameter 104 inputs.

Referring back to FIG. 1, the mode shapes are sent to a modes library 117. As noted above, the mode shapes are fixed functions for a given part regardless of the state parameters 104; that is, the mode shapes reflect an inherent, fundamental frequency content of the part being analyzed. The mode amplitudes 114, however, change as the state parameters 104 change, making it possible to deduce mode amplitudes 114 based the state parameters 104. The mode amplitudes 114 are inputs of a multiple-input/multiple-output (MIMO) model 116 for which measured state parameters (after being pre-processed) also serve as inputs. The MIMO model 116 receives model input parameters 118 that are derived from the measured state parameters 104. The mode amplitudes 114 and the model input parameters 118 obtained from known measured state parameters 104 are collectively called "training data" because they train the MIMO model 116 to output a given set of mode amplitudes 114 in response to measured model input parameters 118.

In one example, during the preprocessing step 120, the measured state parameters 104 are transformed from the time domain into the revolution domain to obtain model input parameters 118 that are in the same domain as the mode amplitude 114. In one example, the state parameters 104 are pre-processed (e.g., scaled, low-pass or band-pass filtered, interpolated, etc.) to create model input parameters 118 for the model. The preprocessing step 120 may include linear and non-linear transformations, computation of interaction parameters, etc. The result is a set of model input parameters 118, or predictors, that are in matrix form parameterized by revolution number and that can be used as model inputs during signal estimation. Each column of the matrix in this example corresponds to the time history of one input parameter.

The model input parameters 118 and the mode amplitudes 114 are then fitted into the MIMO model 116 to define relationships between the state parameters 104 and the mode amplitudes 114, which in turn are related to the load on the part. The MIMO model 116 ties the state parameters 104 and the mode amplitudes 114 through any desired appropriate relationship (e.g., linear or non-linear, static or dynamic).

Note that the MIMO model 116 does not need to be a single model or have a single specific form. For example, the estimation model may include a global model 121 and one or more local models 122. The global model 121 is simply a model that is a single representation of the relationship between state parameter inputs and the load signal outputs. That is, the global model 121 acts as a single feature space that is used for signal estimation in all or many operating conditions. Although the global model 121 can provide useful overall information about the load, it may be desirable to also create more precise models that better reflect the load under specific sets or domains of operating conditions or regimes.

To do this, the training data (i.e., the model input parameters 118 and the mode amplitudes 114) may be partitioned into domains or regimes so that separate local models 122 may be developed for each domain or regime. These local models 122 in essence act as individual feature spaces, each space representing a different operating condition of the part or a group of closely-related conditions referred to herein as domains or regimes. Increased accuracy can be obtained through appropriate partitioning to allow different local models 122 to be used in different regimes. For example, in a rotorcraft application, the data may be partitioned according to flight regime (i.e., a given flight maneuver) because different regimes will generate different patterns of dynamic loads on the part and thereby generate different mode shapes and/or amplitudes warranting different estimated loads. The training data may also be partitioned based on aircraft configuration.

Note that different local models 122 for the same part may vary in both their mode shapes and model coefficients or only in their model coefficients. A regime recognition step 302 may be used to determine when individual local models should be used. Regime recognition may also be incorporated as a separate modeling layer in the estimation model 106 so that it will use the same state parameters 104 to determine which local model to use. Although it is possible to use the global model 121 or the local models 122 alone, using both provides higher quality information and also allows detection of anomalous conditions, particularly when the estimated load generated by one model does not match the estimated load generated by the other model.

A model coefficient library 124 is then generated from the MIMO model 116. The model coefficient library 124 acts as a map that defines the relationships between the input parameters 118 and the mode amplitudes 114. In one example, the model coefficient library 124 contains coefficients of a linear regression model. The model coefficient library 124 and the modes library 117 together act as the hybrid virtual sensor estimation model 106 used to infer loads from measured state parameters 104 that are input into the estimation model 106.

To ensure that the estimation model is robust for a broad range of equipment configurations and operating conditions, load measurements and state parameter measurements are conducted for a set of selected representative equipment configurations and operation conditions. Model training is ideally performed using statistically representative data.

Once the estimation model 106 has been trained by the model training 102, the estimation model 106 can generate estimated loads from new measured state parameters 104 by inferring output signal waveforms (e.g., load signal waveforms) from the state parameters 104. The final results of model training include the modes library 117 containing mode shapes, the coefficients library 124 containing coefficients of the model, an algorithm that realizes the MIMO model 116 using the coefficient library 124, a pre-processing algorithm to process raw state parameters 104 to form the model input parameters 118, and a load reconstruction algorithm 156 that synthesizes an estimated signal output waveform from the mode shapes and the estimated mode amplitudes.

Application of the estimation model 106 to generate an estimated signal output starts by pre-processing the measured state parameters 104 in a pre-processing step 150 in the manner noted above to obtain model input parameters 152. The model input parameters 152 are then sent to a mode amplitudes estimation step 154. In this step, the model input parameters 152 are mapped to estimated model amplitudes by applying the MIMO model 116 algorithm with model coefficients library 124 to obtain estimated mode amplitudes.

The estimated mode amplitudes are then sent to a load reconstruction step 156 where they are combined with mode shapes from the modes library 117 to synthesize the estimated load waveform 158. Note that there may be cases where the estimation model 106 needs to take into account measured state parameters 104 that fall outside of the range of the training data used to generate the estimation model 106. In this case, it is possible to obtain the mode amplitudes corresponding to the out-of-range state parameters 104 in the same way as described above, particularly if the MIMO model 116 is a linear map. Moreover, any available direct load measurements of loads, even on a temporary basis, may be used as feedback to the estimation model 106 to update and customize the estimation model 106 based on actual operation of the particular system (e.g., aircraft, further improving the fidelity of the estimation models 106.

By constructing estimated load signals from measured state parameters, virtual load sensing can be conducted without actually using physical load sensors 110*a* on the parts of interest. The physical sensors 110*a* are replaced with virtual load sensors using measurements that are easier and more efficient to obtain. The physical sensors 110*b* (and optionally, physical sensors 110*c*) are then used to calibrate, update and validate the estimation model, as an input to the model and to modify the model during equipment operation, as will be described below.

Figure 3:
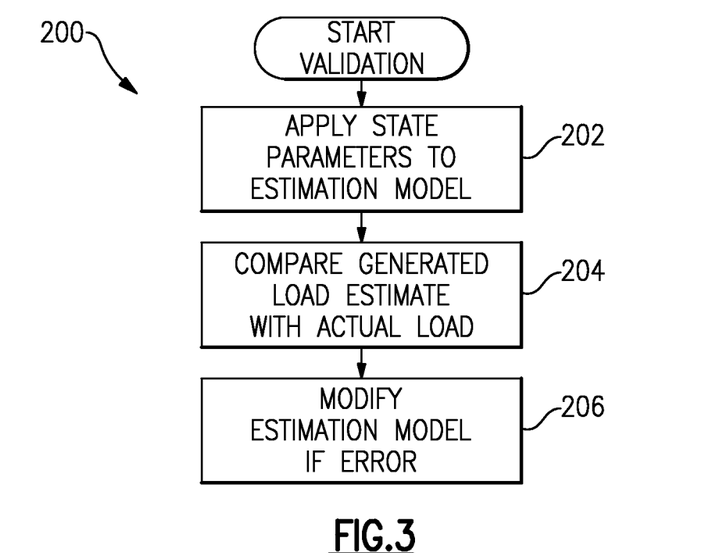
FIG. 3 is a block diagram illustrating a model validation process according to one embodiment of the invention.

Once the estimated load waveform 158 has been obtained, the estimated load 158 may undergo a validation process 200 as shown in FIG. 3 to test the accuracy of the estimation and the general robustness of the estimation model 106. The model validation process 200 is an analytical validation and may be conducted as the estimation model 106 is being developed and is conducted again during actual equipment operation. The validation process 200 confirms whether the estimation model 106 is valid for the particular aircraft, flight regime, or other domains or configurations in which the system 100 is actually being used.

For the case where the training/operation physical sensors 110*b* are in the same location and measuring the same loads as during model training, the measured load from physical sensor 110*b* is compared to the estimated load. To test the validity of the estimation model 106, the state parameters 104 corresponding with the measured load from physical sensor 110*b, c* are applied to the estimation model 106 in the manner described above (block 202). Once the estimated load 158 corresponding with the measured state parameters 104 is obtained, the estimated load is compared with the actual measured load (block 204).

Any errors between the estimated load 158 and the actual measured load from physical sensor 110*b, c* are accounted for. The errors themselves reflect inaccuracies in the estimation model 106 that may be due to individual variation between systems (e.g., aircraft) or modification of the systems (e.g., aircraft), such as adding/removing hardware. The errors may be evaluated individually (e.g. using scatter plots) or statistically (e.g. by computing root-mean-square for the error). The estimation model 106 may be updated and modified (block 206) in view of these errors, just for the virtual sensors that correspond to the physical sensors 110*b*, *c*, or optionally for other virtual sensors as well.

If the error exceeds a given threshold, then it may be determined that the estimation model is not applicable for some reason, and it would be desirable to default to a stored set of worst-case damage accumulations for the parts involved or for all of the parts in the system. In other words, in the event that the estimation model appears to be invalid in a particular system (e.g., aircraft) or after a particular operation of the system (e.g., aircraft), then the damage accumulation estimation system returns to the worst-case assumptions, such as are currently used in the prior art. The otherwise somewhat redundant physical sensors 110*b-c* can be used to help determine when the estimation model is invalid beyond adaptation or update, and when to default to the worse-case assumptions.

As another implementation, the adaptive update of the mapping can be further expanded to address adaptive updating of virtual sensor target location feature structure (modes). This update is performed as long-term error metrics are statistically evaluated over a series of missions. The fundamental ingredient is a re-identification of the feature modes of the physical sensor 110*b, c*. This is straightforward because the aircraft state parameters and the actual measurement time history are recorded and available for re-processing. The next step is to propagate the updating of feature structure (modes) for the physical sensor location to the other virtual sensor target locations. This is particularly useful if the system is operated in a new regime or in an existing regime but beyond the original span of the state inputs, neither of which were included in training.

In one implementation, the modes that can be derived from the training/operation physical sensors 110*b* (and optionally operation physical sensors 110*c*) are used to decompose the input signals (measured state parameters 104 and measured signals from physical sensors 110*b, c*) with large dynamic components into their features (modes and amplitudes). Even if the physical sensor 110*b, c* is not at the same location as the input signal, it is likely that the modes would be substantially the same (at least for some physical sensors and virtual sensors). Additionally, the modes derived from the physical sensors 110*b, c* are used to determine the modes that can be used to represent the loads in the virtual sensors. The modes derived from the physical sensor 110*b, c* are also used to decompose the signal from the physical sensor 110*b, c*, so that the amplitudes can be used as inputs to the virtual sensor model.

As another implementation for the physical sensors 110*b* (and optionally physical sensors 110*c*), the physical sensor measurement can be pre-processed to explicitly compute the feature amplitudes for that physical sensor location (based upon the measured time history and the previously stored feature structure). In this implementation, the measured signals from the physical sensor 110*b, c* is in essence thus converted to a set of derived system state parameters. The addition of the physical sensor measurement, which is more strongly correlated to the measurements from the virtual target sensors, as an input increases the accuracy of predictions of measurements of the virtual sensor target locations.

A given hybrid virtual sensor estimation model may reflect the outputs of multiple sensors instead of a single sensor and derive features that reflect the output signals of the multiple sensors. This results in a composite estimated signal corresponding to the measurements of multiple sensors. In this case, each sensor will have its own associated sensor-specific model with its own independent mode shapes and mode amplitudes (i.e., their own independent features). More particularly, the features associated with each sensor act as the sensor-specific model to reflect the measurement of that sensor. The sensor-specific mode shapes associated with each sensor are then combined to form composite mode shapes that describe the entire set of loads experienced by the multiple sensors simultaneously.

The composite mode shapes can be chosen to allow the load signals of multiple sensors to be described by only one set of mode amplitudes rather than multiple sets of independent mode amplitudes corresponding to each sensor. This creates a more robust model by capturing relationships among the virtual sensors, which would not be possible if each model corresponded to only a single sensor. This also allows the model, which maps input parameters into mode amplitudes to be more compact and efficient than if estimating the output of each load sensor individually. Combining sensor-specific models of multiple sensors in a single estimation model also allows monitoring of time-dependencies within the estimation model.

In one example, mode shapes for multiple load sensors having a unique set of mode amplitudes as described above were obtained by stacking matrices in the model corresponding to individual loads together vertically (i.e., along the azimuth angle dimension) to form a composite matrix. In one example, mode shapes and mode amplitudes are obtained from this matrix using singular value decomposition as described above for the case of single sensor. Note that mode shapes obtained here are extended mode shapes that can be broken into individual mode shapes for each sensor. MIMO model 116 is then developed using input parameters derived from state parameters as inputs and computed mode coefficients as outputs.

The estimation process is then conducted in the manner described above from the measured state parameters 104, applying the inputs derived from the state parameters into the integrated multi-sensor model. As described above, the mode shape obtained in model training is split into separate mode shape groups, each mode shape group corresponding to one of the discrete loads. Note that the number of mode amplitudes in this case does not increase because each load is a result of the same state parameters, resulting in the same mode amplitudes; only the mode shapes for each load are different.

Figure 4:
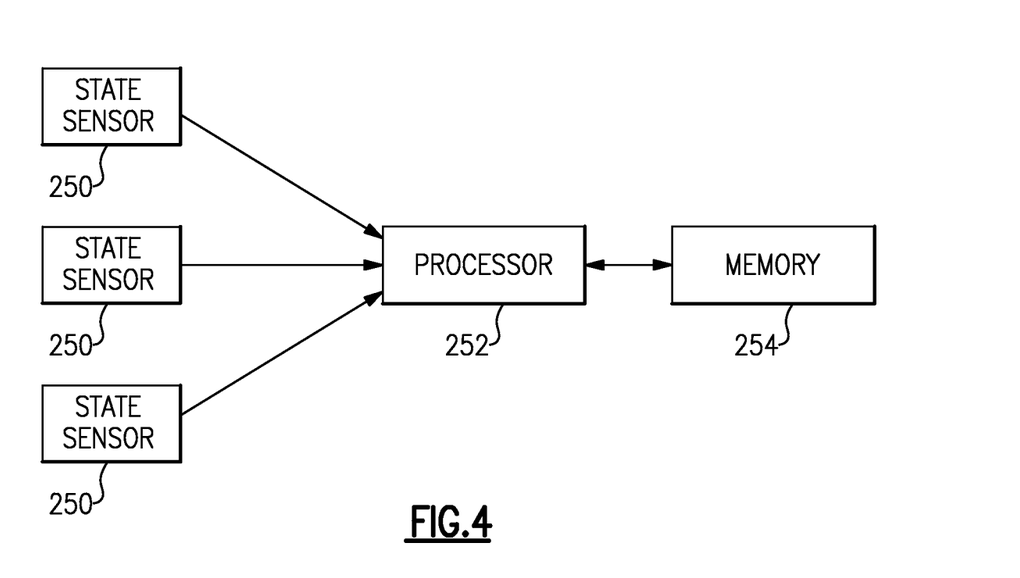
FIG. 4 is a representative diagram of a system that conducts the signal estimation process according to one embodiment of the invention.

The load estimation system 100 described above can be conducted in any appropriate system hardware and software without departing from the scope of the invention. As shown in FIG. 4, input state parameters may be measured through any desired sensors 250 as well as other input sources, or derived from the physical sensors 110*b* (and optionally, physical sensors 110*c*) and sent to a processor 252. The processor 252 conducts the pre-processing step 150, the mode amplitudes estimation step 154, and the load reconstruction step 158 by retrieving mode coefficients and mode shapes from their respective libraries 117, 124, which are stored in one or more memory devices 254.

The physical locations of the various components of the hybrid virtual sensor estimation system are not critical to the operation of the system. Any or all of the components may be, for example, off-board (e.g., on the ground), on-board (e.g., on an aircraft), or any combination of the two.

Note that even though the examples above assume that a part is actually operating while the load signals are being obtained to generate the model, the model can be obtained through a simulated part operation as well without departing from the scope of the invention.

3. Potential Load Monitoring Applications

Although the above examples focus on virtual sensing and monitoring of loads containing harmonic content with respect to rotorcraft, those of skill in the art will recognize that the method and system described above may be used in any application that experiences quasi-periodic characteristics, such as jet engines, HVAC chillers, electric motors, optical applications, etc., without departing from the scope of the invention. Also, the inventive estimation process may be used to estimate signals in fixed, non-rotating parts as well (i.e., signals having mode shapes with either simple frequency content or no frequency content).

Moreover, the information obtained through the load monitoring system and method described above is accurate and detailed enough to be used for conducting various fleet management and design functions. Possible applications include, for example, calculations of remaining retirement time or useful life in the part based on the estimated loads, life-extending control that informs a user when he or she is entering a regime that is potentially damaging to the equipment so that the user can either back off or allow the flight control system to change operation to minimize the damaging conditions. In aircraft applications, for example, the load monitoring may also be used for usage-based or condition-based fleet management, in which equipment maintenance is based on the load monitoring and actual usage information rather than simply flight hours or cycles (e.g., ground-air-ground) of usage. This allows customization of maintenance to the actual conditions encountered by the equipment, reducing overall maintenance time and costs. Over time, the equipment structural design may be optimized according to the anticipated loads they may encounter, thereby allowing loads to be less conservative and avoid unneeded over-design of parts. The load monitoring also provides the ability to estimate loads easily during equipment operation.

It should be understood that various alternatives to the embodiments of the invention described herein may be employed in practicing the invention. It is intended that the following claims define the scope of the invention and that the method and apparatus within the scope of these claims and their equivalents be covered thereby.

The invention claimed is:

1. A method for monitoring loads in a system having a plurality of components including a target component, the method comprising:

obtaining an input state parameter of the system;

receiving a physical sensor signal from a physical sensor monitoring at least one of the components in the system, wherein the physical sensor signal varies more quickly than the input state parameter, and contains more dynamic content than the input state parameter; and providing during equipment operation the physical sensor signal and the input state parameter as inputs to a hybrid virtual sensor estimation model after a model training phase in which the hybrid virtual sensor estimation model is created and trained utilizing at least one training physical sensor, the at least one training physical sensor not being utilized during the equipment operation;

wherein the hybrid virtual sensor estimation model outputs a plurality of virtual sensor signals based on the inputs, and each of the virtual sensor signals represents an estimate of a load or response being experienced at a different respective location on one or more of the plurality of components, including the target component.

2. The method of claim 1 wherein the physical sensor is one of a plurality of physical sensors, each monitoring a load or response at different locations on one or more components in the system.

3. The method of claim 2 further including the step of determining damage accumulation or estimated retirement time of one or more of the plurality of components based upon the estimates of the loads over time.

4. The method of claim 3 wherein features of the physical sensor signal include modes of the physical sensor signal, and wherein the load is characterized in terms of at least some of the modes of the physical sensor signal in the determining of the load on the target component.

5. The method of claim 1:

wherein the system is an aircraft;

wherein the input state parameter comprises one of speed, weight, attitude, torque, rate of climb, vibration, and pilot controls of the aircraft; and wherein the physical sensor signal comprises a strain of the aircraft.

6. The method of claim 1, wherein the physical sensor signal is directly related to the target component, and the input state parameter is indirectly related to the target component.

7. The method of claim 1:

wherein a plurality of different input state parameters of the system are obtained and provided as inputs to the estimation model after the estimation model has been created; and wherein the load on the target component is determined based upon the plurality of different input state parameters.

8. The method of claim 1, wherein the physical sensor signal is used to modify the hybrid virtual sensor estimation model during equipment operation.

9. The method of claim 1, wherein the hybrid virtual sensor estimation model utilizes a model coefficient library and a modes library.

10. The method of claim 1 further comprising comparing an estimated load output by the hybrid virtual sensor estimation model to a measured load.

11. The method of claim 10 further comprising updating the hybrid virtual sensor estimation model in response to an error between the estimated load and the measured load exceeding a threshold.

12. An estimator of a load in a system comprising:

a physical sensor measuring a physical load on the system during operation; and a hybrid virtual sensor estimation model that maps a relationship between inputs and a plurality of estimated loads;

wherein the physical load and input state parameter are provided during equipment operation as inputs to the hybrid virtual sensor estimation model after a model training phase in which the hybrid virtual sensor estimation model is created and trained utilizing at least one training physical sensor, the at least one training physical sensor not being utilized during the equipment operation;

wherein each of the plurality of estimated loads is an estimate of a load being experienced at a different respective location on one or more of a plurality of components in the system;

wherein the hybrid virtual sensor estimation model maps the input state parameter and the physical load to the plurality of estimated loads.

13. The estimator of claim 12 wherein the physical sensor is one of a plurality of physical sensors, each measuring a load or response at different locations on one or more components in the system.

14. The estimator of claim 12 wherein the estimator is configured to calculate loads at one or more locations in the system by using physics based models to transfer one or more virtual sensor loads to other locations in the system.

15. The estimator of claim 12, wherein the physical sensor is used to modify the hybrid virtual sensor estimation model during the equipment operation.

16. The estimator of claim 12, wherein the hybrid virtual sensor estimation model utilizes a model coefficient library and a modes library.

17. The estimator of claim 12, wherein an estimated load output by the hybrid virtual sensor estimation model is compared to a measured load.

18. The estimator of claim 17, wherein the hybrid virtual sensor estimation model is updated in response to an error between the estimated load and the measured load exceeding a threshold.

* * * * *